United States Patent [19]

Lew

[11] Patent Number: 5,193,400

[45] Date of Patent: * Mar. 16, 1993

[54] UNIVERSAL ROTAMETER

[76] Inventor: Hyok S. Lew, 7890 Oak St., Arvada, Colo. 80005

[*] Notice: The portion of the term of this patent subsequent to Feb. 16, 2010 has been disclaimed.

[21] Appl. No.: 749,981

[22] Filed: Aug. 26, 1991

Related U.S. Application Data

[63] Continuation-in-part of Ser. No. 698,296, May 10, 1991.

[51] Int. Cl.$^5$ .............................................. G01F 1/24
[52] U.S. Cl. ................................ 73/861.56; 73/861.57; 73/440
[58] Field of Search ............ 73/861.55, 861.56, 861.57, 73/861.53, 861.54, 195, 32 R, 440

[56] References Cited

U.S. PATENT DOCUMENTS

| | | | |
|---|---|---|---|
| 2,441,350 | 5/1948 | Fischer | 73/861.57 |
| 2,490,792 | 12/1949 | Fischer | 73/861.57 |
| 4,542,650 | 9/1985 | Renken et al. | 73/196 |
| 4,630,485 | 12/1986 | Wastl, Sr. | 73/861.57 |
| 4,653,321 | 3/1987 | Cunningham et al. | 73/197 |
| 4,787,253 | 11/1988 | deFassell et al. | 73/861.54 |
| 4,873,872 | 10/1989 | Wechsler | 73/861.57 |

Primary Examiner—Herbert Goldstein

[57] ABSTRACT

A rotameter comprises a vertically disposed flow passage with cross sectional area progressively increasing from the lower inlet to the upper outlet thereof, and a float suspended in the flow passage and guided by a plurality of ridge-like float guides disposed parallel to and axisymmetrically about the central axis of the flow passage, which float guides keep the float suspended in the fluid stream in a coaxial relationship to the flow passage, wherein a float position indicator disposed within an elongated groove included in one of the float guides following the guiding edge thereof moves with float in vertical directions due to the magnetic attraction therebetween created by a permanent magnet included in either the float or the float position indicator, and provides an electrical signal representing the vertical position of the float, from which the flow rate of the fluid moving through the flow passage is determined. A pair of rotameters respectively having two floats with different values of the weight to volume ratio installed in a series arrangement provides a three-in-one rotameter that simultaneously determines the mass and volume flow rates of the fluid and the density of the fluid as functions of the vertical positions of the two floats respectively included in the two rotameters.

14 Claims, 3 Drawing Sheets

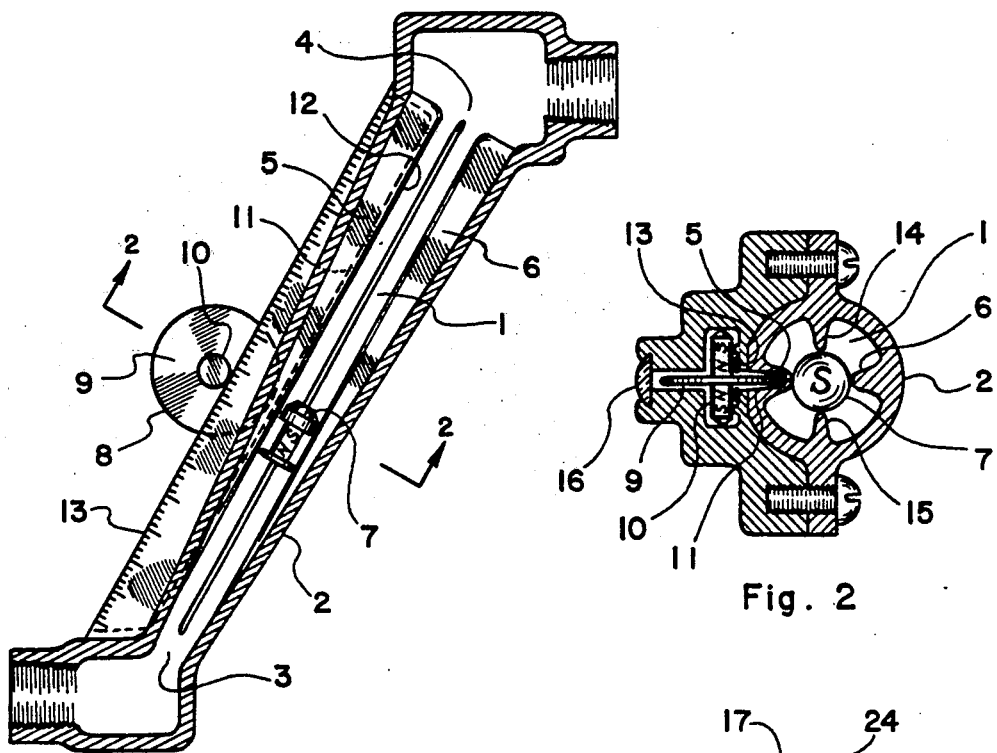
Fig. 1
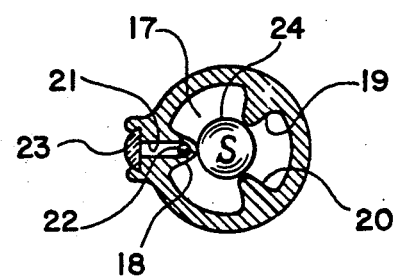
Fig. 2
Fig. 3
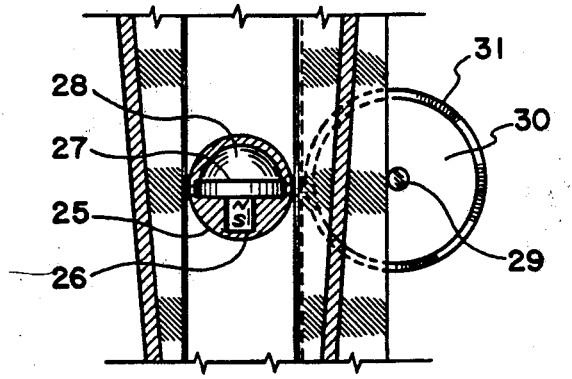
Fig. 4
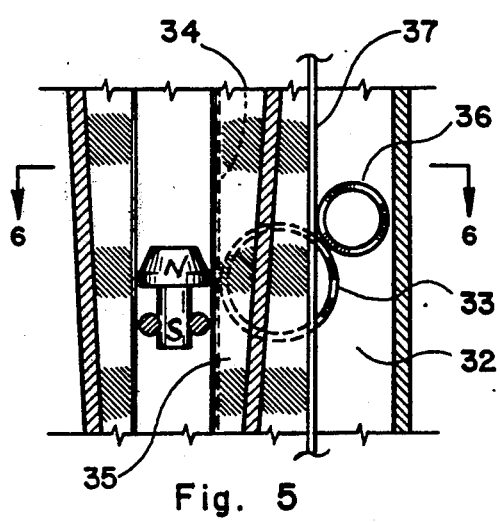
Fig. 5

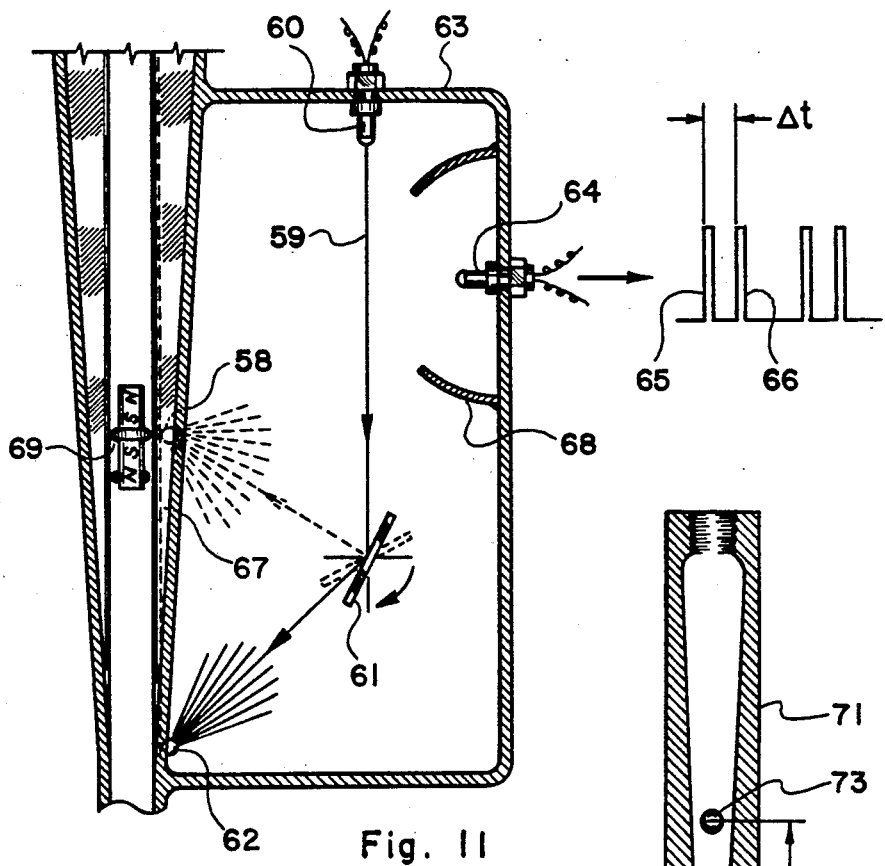
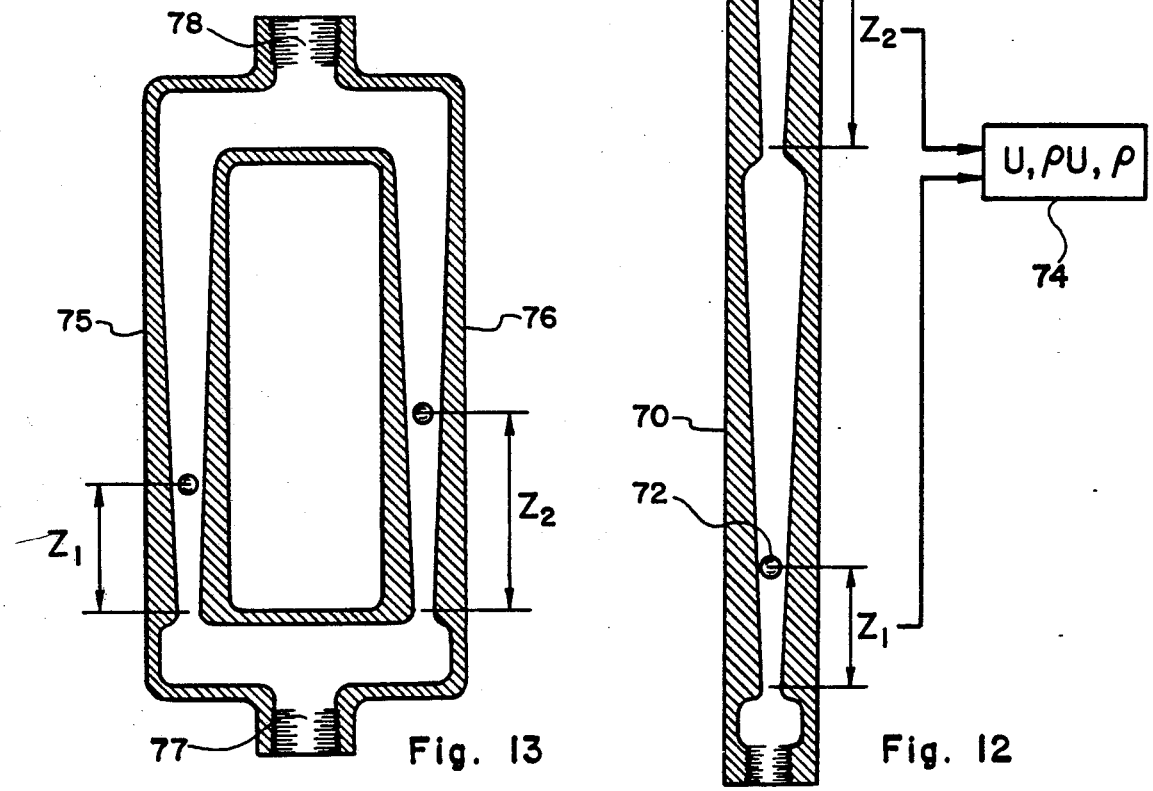

UNIVERSAL ROTAMETER

This patent application is a continuation-in-part to patent application Ser. No. 07/698,296 entitled "ROTAMETER WITH FLOAT GUIDES" filed on May 10, 1991, and consequently, the priority of the invention described and claimed in the present patent application is based on the aforementioned parent patent application.

BACKGROUND OF THE INVENTION

The rotameters comprising a vertically disposed tapered flow passage including a float suspended therein, wherein the vertical position of the float relative to a reference section located at the bottom inlet extremity of the tapered flow passage indicates the amount of flow rate, are widely employed in industries and scientific laboratories, which provide flow measurement with excellent accuracy and reliability. There are a number of short-comings in the existing versions of the rotameters which are, firstly, the lack of an accurate and reliable electronic read-out device incorporated into the rotameter that provides the information on the flow rate in the form of an electrical signal which can be fed into flow computers or flow control devices, and secondly, measuring flow of different fluids requires different rotameters custom calibrated to the specific fluid under measurement and, consequently, no rotameter available at the present time is capable of measuring flow of fluid with varying density.

BRIEF SUMMARY OF THE INVENTION

The primary object of the present invention is to provide a rotameter that can be installed in an up-right or a tilted position, whereby the same rotameter can be used to measure fluid flows of different velocity ranges or flow of fluids with different density by merely changing the tilt angle of the rotameter installation.

Another object is to provide a rotameter comprising a plurality of float guides disposed parallel to the central axis of the tapered passage of the rotameter, which float guides confines the float to the central portion of the cross section of the tapered flow passage in a freely slidable arrangement in directions parallel to the central axis of the tapered flow passage.

A further object is to provide the rotameter with the plurality of float guides described in the aforementioned object of the present invention, wherein at least one of the plurality of float guides includes a elongated cavity disposed parallel to the guiding edge thereof, which elongated cavity accommodates a float position indicator following the float in rolling motion by means of magnetic attraction therebetween.

Yet another object is to provide the rotameter described in the aforementioned object of the present invention, that comprises electrical read-out device providing the information on the position of the float position indicator in the form of an electrical signal.

Yet a further object is to provide the rotameter described in the aforementioned object of the present invention, that comprises an optical device providing the information on the position of the float position indicator.

Still another object of the present invention is to provide a three-in-one rotameter comprising a pair of rotameters installed in a series arrangement, wherein the two floats respectively included in the two rotameters have two different values of the weight-to-volume ratio, which three-in-one rotameter determines the mass and volume flow rates as well as the density of fluid as functions of the positions of the two floats.

Still a further object of the present invention is to provide a three-in-one rotameter comprising a pair of rotameters installed in a parallel arrangement bifurcating the flow, wherein the two floats respectively included in the two rotameters have two different values of the weight-to-volume ratio, which three-in-one rotameter determines the mass and volume flow rates as well as the density of fluid as functions of the positions of the two floats.

These and other objects of the present invention will become clear as the description thereof progresses.

BRIEF DESCRIPTION OF FIGURES

The present invention may be described with a greater clarity and specificity by referring to the following figures:

FIG. 1 illustrates a cross section of an embodiment of the rotameter with float guides, that also includes a float position indicator disposed in an elongated cavity included in one of the float guides, which float position indicator follows the float in a rolling motion by means of magnetic attraction therebetween.

FIG. 2 illustrates another cross section of the embodiment shown in FIG. 1.

FIG. 3 illustrates a cross section of another embodiment of the rotameter with float guides, which cross section is taken along a plane perpendicular to the central axis of the tapered flow passage of the rotameter.

FIG. 4 illustrates a cross section of a further embodiment of the rotameter with float guides, which cross section is taken along a plane including the central axis of the tapered passage of the rotameter.

FIG. 5 illustrates a cross section of yet another embodiment of the rotameter with float guides.

FIG. 11 illustrates another embodiment of an optical device providing the position of the float position indicator.

FIG. 12 illustrates a cross section of an embodiment of the three-in-one rotameter.

FIG. 13 illustrates a cross section of another embodiment of the three-in-one rotameter.

DESCRIPTION OF THE ILLUSTRATED EMBODIMENTS

Figure 6:
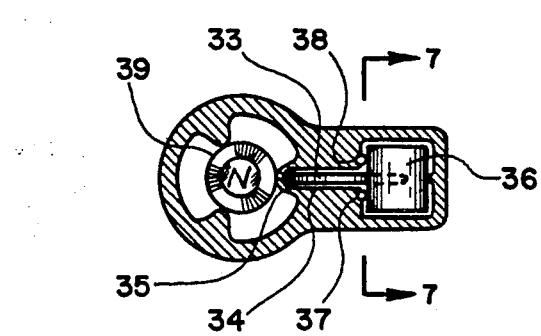
FIG. 6 illustrates another cross section of the embodiment shown in FIG. 5.

In FIG. 1 there is illustrated a cross section of an embodiment of the rotameter with float guides constructed in accordance with the principles of the present invention, which cross section is taken along a plane including the central axis of the tapered flow passage 1 included in the rotameter body 2. The tapered flow passage 1 with cross sectional area progressively increasing from the lower inlet 3 to an upper outlet 4 has a plurality of elongated float guides 5, 6, etc., of ridge-like or fin-like construction disposed parallel to and in a substantially axisymmetric arrangement about the central axis of the tapered flow passage 1, which float guides confines the movement of the float 7 suspended in the tapered flow passage 1 in directions parallel to the central axis of the tapered flow passage 1. As a consequence, the tapered flow passage 1 can be disposed in a perfectly vertical position or in a tilted position. It should be understood that the float guides may be made of a plurality of stiff elongated rods disposed parallel to the central axis of the tapered flow passage 1 in an axisymmetric arrangement. In general, the volume flow rate V of the fluid moving through the tapered flow passage 1 is related to the vertical position z of the float measured from a reference section located at the lower extremity of the tapered flow passage 1 by equation $$\dot{V} = f(z)\sqrt{\frac{2}{C_D}\left(\frac{W}{\rho} - V\right)\cos\theta} , \quad (1)$$

where f(z) is an empirically determined function with independent variable z, $C_D$ is the drag coefficient of the float 7, W and V are respectively the weight and volume of the float 7, $\rho$ is the density of the fluid, and $\theta$ is the tilt angle of the tapered flow passage 1 between the vertical axis and the central axis of the tapered flow passage 1. A well designed rotameter has the function f(z) that increases linearly with z, and equation (1) reduces to $$\dot{V} = Cz\sqrt{\frac{2}{C_D}\left(\frac{W}{\rho} - V\right)\cos\theta} , \quad (2)$$

where C is an empirically determined coefficient of proportionality. It is readily recognized from equations (1) and (2) that the sensitivity of the rotameter can be increased by increasing the tilt angle $\theta$. When the rotameter body 1 is made of a transparent plastic material or glass, the value of z can be read by direct observation and the flow rate of fluid can be determined therefrom. In applications dealing with flow of fluid of toxic nature, or those at high temperature or pressure, the rotameter body 1 must be made of a strong metal such as a stainless steel or other alloy steels or metals. In such cases, the rotameter must have a remote read-out device, that provides the position of the float disposed within the tapered flow passage 1 having an opaque metallic wall. In the present invention, the remote read-out device comprises the magnetized float 7 and a float position indicator 8 comprising a disc 9 with a ferromagnetic rim thereof rolling on an axle 10 that may include one or more permanent magnets. The disc 9 engages a narrow groove 11 with bottom disposed at a close proximity to the guiding edge 12 of one of the float guides. The float 7 including a permanent magnet has an enlarged downstream end made of a ferromagnetic metal that attracts the ferromagnetic rim of the disc 9. When the tapered flow passage 1 is disposed in a tilted position, the float 7 must have an enlarged upstream end made of nonmagnetic material or of thin ferromagnetic material in order to keep the float 7 at a coaxial position with the central axis of the tapered flow passage 1. Of course, the ferromagnetic and nonmagnetic enlarged ends of the float 7 can be reversed from the illustrative embodiment shown. The magnetic attraction between the enlarged downstream end of the float 7 and the ferromagnetic rim of the disc 9 makes the disc 9 follow the movement of the float 7 in rolling motion. The position of the float 7 can be determined by manually observing the position of the axle 10 on the scales 13, or by other electrical means providing an electrical signal representing the position of the axle 10 on the scale 13. When the axle 10 is made of one or more permanent magnet as shown in FIG. 2, the entire disc 9 must be made of a ferromagnetic material.

In FIG. 2 there is illustrated another cross section of the embodiment shown in FIG. 1, which cross section is taken along plane 2—2 perpendicular to the central axis of the tapered flow passage 1 as shown in FIG. 1. The float guide 5 including the groove 11 accommodating the disc 9 of the float position indicator 8 must have a thickness necessary to incorporate the groove 11 thereinto, while the other float guides 6, 14 and 15 may have a thin construction. In the particular illustrative embodiment shown the float guide 6 is made to a thickness matching that of the float guide 5 in order to establish an axisymmetric arrangement of the float guides about the central axis of the tapered flow passage 1. Instead of the combination of four float guides shown, a combination of three float guides may be employed as shown in FIG. 3. The position of the axle 10 on the scale 13 is read through the transparent window 16. When the diameter of the tapered flow passage 1 is relatively small, only a permanent magnet of small diameter can be included in the float 7, wherein the permanent magnet may not provide a sufficient magnetic force to move the disc 9 therewith. In such a case, the axle 10 includes a pair of permanent bar magnets coaxially disposed on the two opposite sides of the ferromagnetic disc 9 in a mutually repulsing pole arrangement, wherein the magnetic flux from both permanent magnets directed through the ferromagnetic disc 9 boosts the magnetic attraction between the float and the disc 9 ensuring the unified movement therebetween. In general, either one of the float 7 or the float position indicator 8 may include one or more permanent magnets, or both thereof may include permanent magnets.

In FIG. 3 there is illustrated a cross section of another embodiment of the rotameter with float guides, which cross section equivalent to that shown in FIG. 2 is taken along a plane perpendicular to the central axis of the tapered flow passage 17 of the rotameter, which has three ridge-like or fin-like float guides 18, 19 and 20, one 18 of which float guides includes a groove 21 accommodating the float position indicator 22 of a spherical shape of solid or hollow construction made of a ferromagnetic material. The position of the float position indicator 22 can be obtained by manually reading the scale disposed following the bottom of the groove 21 through the transparent cover 23. The float 24 may have the construction shown in FIG. 4 or 5 or 11.

In FIG. 4 there is illustrated a cross section of a further embodiment of the rotameter with float guides, which cross section is taken along a plane including the central axis of the tapered flow passage. This rotameter has essentially the same construction as that shown in FIGS. 1 and 2 with one exception in the shape of the float 25, that has now a spherical shape. The float 25 includes a permanent magnet 26 with a ferromagnetic disc 27 in contact with one extremity thereof. The ferromagnetic disc 27 divides the interior of the spherical float 25 into the solid lower half including the permanent magnet 26, and the hollow upper half 28, which arrangement keeps the float at a position wherein the ferromagnetic disc 27 is kept at a horizontal plane and maintains the maximum magnetic attraction between the float 25 and the float position indicator 29 with the disc 30 having a rim ferromagnetic ring 31. The hollow cavity 28 included in the float 28 also increases the sensitivity of the rotameter measuring liquid flow by creating a buoyancy force counteracting the weight of the float. In order to increase the buoyancy force of the float, a hollow downstream extension may be added to the float, or the float may be constructed in an oblong shape that includes a large hollow cavity in the downstream half thereof.

In FIG. 5 there is illustrated a cross section of yet another embodiment of the rotameter with float guides, which cross section is taken along a plane including the central axis of the tapered flow passage of the rotameter. This rotameter has essentially the same construction as that of the embodiment shown in FIGS. 1 and 2 with one exception in the float position guide 32, which comprises a ferromagnetic ring 33 rolling on the bottom of the groove 34 included in one 35 of the plurality of float guides, and a hollow cylindrical shell 36 made of a ferromagnetic material in contact with the outer ring of the ferromagnetic ring 33 and rolling on a pair of rails or ohmic resistance wires 37 and 38.

In FIG. 6 there is illustrated another cross section of the embodiment shown in FIG. 5, which cross section is taken along a plane 6—6 perpendicular to the central axis of the tapered flow passage of the rotameter as shown in FIG. 5. The enlarged extremity of the magnetized float 39 attracts the ferromagnetic ring 35 thereto. The magnetic flux from the magnetized float 39 now directed through the ferromagnetic ring 33 attracts the ferromagnetic cylindrical shell 36 to the ferromagnetic ring 33. As a consequence, the ferromagnetic cylindrical shell 36 becomes seated on the pair of rails or ohmic resistance wires 37 and 38. It is self evident that the ferromagnetic ring 33 and the ferromagnetic cylindrical shell 36 follow the movement of the magnetized float 39. The ferromagnetic cylindrical shell 36 may be replaced with a pair of cylindrical shell or solid bar permanent magnets joined coaxially to one another in a mutually repulsing pole arrangement. In the particular illustrative embodiment shown, the two cylindrical or bar magnets must be joined in S pole to S pole arrangement in order to establish the maximum magnetic attraction between the enlarged N pole of the float and the float position indicator 32. It is readily recognized that the ferromagnetic cylindrical shell 36 may also be replaced with a hollow ferromagnetic sphere.

Figure 7:
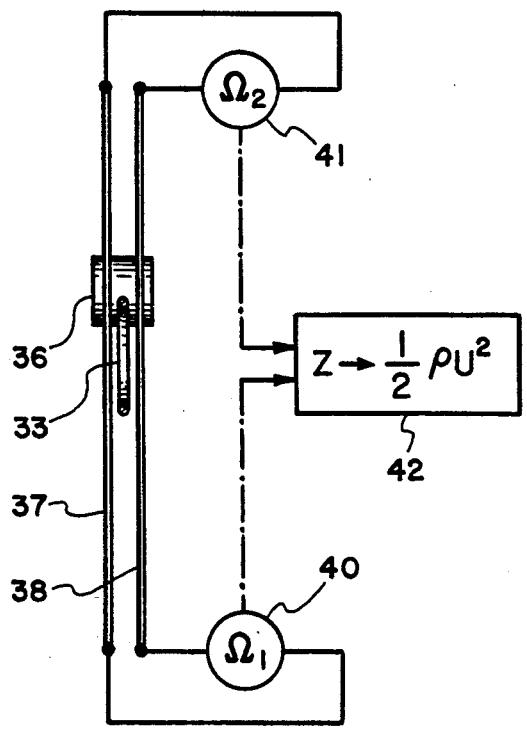
FIG. 7 illustrates a further cross section of the embodiment shown in FIGS. 5 and 6, that illustrates an embodiment of the electrical device that provides the position of the float in the form of an electrical signal.

In FIG. 7 there is illustrated a cross section of the embodiment shown in FIGS. 5 and 6, which cross section taken along plane 7—7 as shown in FIG. 6 illustrates the operating principles of an embodiment of the remote read-out device providing the information on the position of the float position indicator 32 in the form of an electrical signal. The ferromagnetic or magnetic cylindrical shell or roller 36 rolling on the pair of ohmic resistance wires 37 and 38 establishes an electrical connection between the two wires 37 and 38, wherein at least one of the two wires 37 and 38 disposed parallel to the central axis of the tapered flow passage has a high specific ohmic resistance. When both wires or rails have a specific ohmic resistance value equal to $\Omega_S$, the relative position z of the cylindrical shell or roller 36 intermediate the two extremities of the pair of wires or rails 37 and 38 is given by equation $$\frac{z}{z_0} = \frac{\Omega_1 - \Omega_2}{4\Omega_S z_0} + \frac{1}{2}, \qquad (3)$$

where $z_0$ is the length of the combination of the two wires or rails 37 and 38, and $\Omega_1$ and $\Omega_2$ are two measured values of the ohmic resistance respectively measured by the ohm meters 40 and 41. In deriving equation (3), it is assumed that the lead wires connecting the ohm meters 40 and 41 respectively to the two extremities of the pair of wires or rails 37 and 38 have negligibly small ohmic resistances, and the contact resistances arising from the imperfect contact between the cylindrical shell or roller 36 and the wires or rails 37 and 38 are eliminated, whereby the relative position of the cylindrical shell or roller 36 is independent of the actual value of the contact resistance. It is readily recognized that $\Omega_1$ and $\Omega_2$ are respectively the ohmic resistances of two opposite portions of the pair of ohmic resistance wires or rails 37 and 38 located on the two opposite sides of the cylindrical shell or roller 36, respectively. A data processor 42 determines the position of the float 39 from the numerical values of $\Omega_1$ and $\Omega_2$ supplied thereto and then determines the dynamic pressure of the fluid flow, that is equal to one half of the fluid density times the square of the fluid velocity, as a function of the position of the float 39. When the fluid density is given or measured by a separate device, the mass flow rate as well as the volume flow rate is determined from the measured value of the dynamic pressure of the fluid flow.

Figures 8, 9:
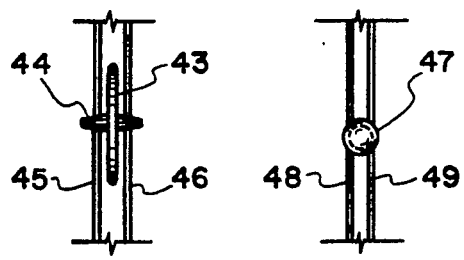
FIG. 8 illustrates another embodiment of the float position indicator employed in an electrical device providing the position of the float in the form of an electrical signal.
FIG. 9 illustrates a further embodiment of the float position indicator employed in an electrical device providing the position of the float in the form of an electrical signal.

In FIG. 8 there is illustrated a modified arrangement of the embodiment shown in FIG. 7. In this embodiment, the float position indicator 43 comprises a ferromagnetic disc or disc with a ferromagnetic rim mounted on a metallic axle 44 rolling on the pair of ohmic resistance wires or rails 45 and 46 instead of the float position indicator including the ferromagnetic ring 33 and the ferromagnetic cylindrical shell or roller 36 shown in FIG. 7. The float position indicator shown in FIG. 8 is essentially the same one as that employed in the embodiment shown in FIGS. 1 and 2, and 4.

In FIG. 9 there is illustrated another modified arrangement of the embodiment shown in FIG. 7. In this embodiment, the float position indicator 44 is a hollow or solid sphere made of a ferromagnetic metal rolling on the pair of ohmic resistance wires or rails 48 and 49, which float position indicator is the same one as that employed in the embodiment shown in FIG. 2.

Figure 10:
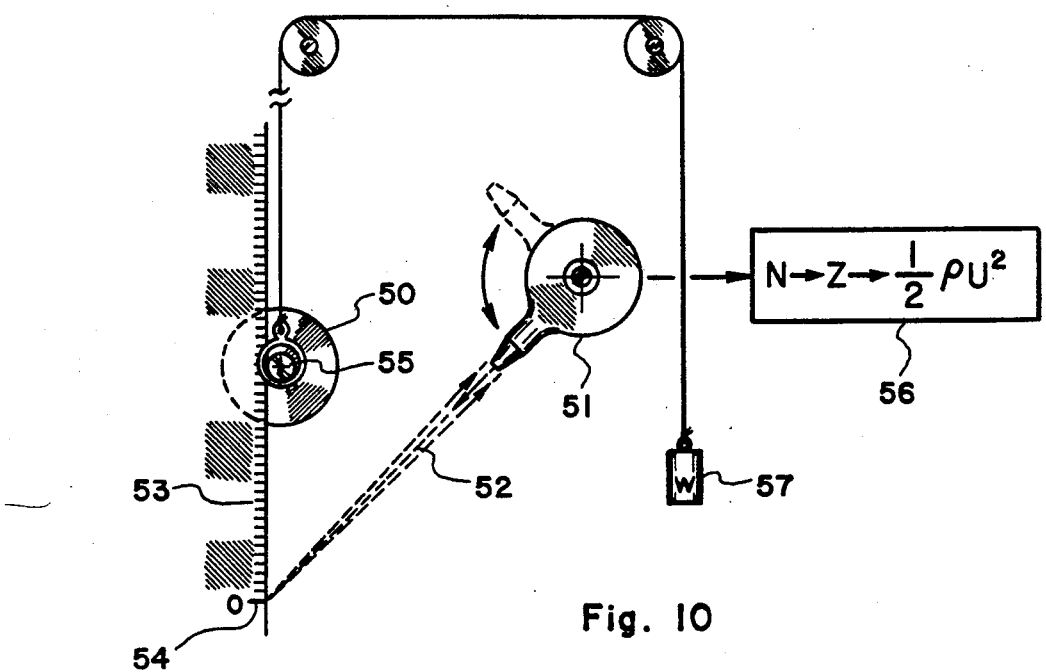
FIG. 10 illustrates an embodiment of an optical device providing the position of the float by reading the number of bar scales indicating the position of the float position indicator.

In FIG. 10 there is illustrated an embodiment of an optical device that reads the position of the float position indicator 50 such as that employed in the embodiments shown in FIGS. 1 and 2, and 4. A bar counter 51 employing a laser beam 52 scanning the bar scales 53 drawn in black color counts the number of the bars between the "zero" section 54 and axle 55 of black color included in the float position indicator 50, which axle 55 is equivalent to a thick bar contrasting the thin bar scales. The bar counter 51 operating much like a bar code reader counts thin bars between the start section 54 and the thick bar 55. A data processor 56 converts the number N of the thin bars between the start section 54 and the axle 55 equivalent to the thick bar into the position z of the float and then determines the dynamic pressure of the fluid flow therefrom as well as the mass or volume flow rate of the fluid. It is evident that the float position indicator 50 comprising a disc and an axle such as those shown in FIGS. 1 and 2, and 3, that is employed in the particular illustrative embodiment shown in FIG. 10, may be replaced with other type of the float position indicator shown in FIG. 2 or 5, that is now painted in black color. A counter weight 57 counter-balancing the weight of the float position indicator 50 may be employed in place of or in conjunction with the partially hollow float such as that shown in FIG. 4. It can be readily recognized that a hollow extension providing the buoyancy force counter-acting the weight of the float can be added to the enlarged end of the float employed in the embodiment shown in FIG. 5 or 11.

In FIG. 11 there is illustrated another embodiment of the optical device reading the position of the float position indicator 58 such as that included in the embodiment shown in FIG. 3, which is polished to reflect the light. A laser beam or a focused light beam 59 emitted from a source 60 is reflected by a rotating or oscillating mirror 61, which light beam is reflected by a reference position marker 62 with light reflecting surface and the float position indicator 58 in sequence during each of the 360 degree rotations of the mirror 61. The interior surface of the sealed chamber 63 is coated with light absorbing black. Therefore, the photodiode 64 receives only the reflected light from the reference position marker 62 or from the float position indicator 58, and produces electrical pulses 65 and 66 respectively corresponding to the light reflected from the reference position marker 62 and the float posion indicator 58. The distance from the reference position marker 62 to the float position indicator 58 is obtained by integrating the angular velocity of the rotating mirror 61 times the distance between the rotating mirror 61 and the bottom of the groove 67 accommodating the float position indicator 58, divided by sine of the angle between the light beam and the bottom of the groove 67, with respect to time over the period $\Delta t$ between the two electrical pulses 65 and 66, which integration can be carried out by a microcomputer included in a data processor that determines the flow data such as the mass or volume flow rate as a function of the position z of the float 50 position indicator so determined. The light shield 68 is employed to cut off the light reflected from the rotating mirror 61 from directly reaching the photodiode 64 without being reflected by the reference position marker 62 or the float position indicator 58. Of course, the float position indicator 58 of spherical shape with polished surface can be replaced with the float position indicator comprising a blackened disc with a light reflecting axle or that comprising a blackened ferromagnetic ring and a light reflecting shell or roller, which are respectively employed in the embodiments shown in FIGS. 2 and 6. It should be noticed that the float 69 includes a pair of permanent magnets respectively affixed to the two opposite sides of a ferromagnetic disc in a coaxial and mutually repulsing pole arrangement. A buoyancy providing hollow extension may be affixed to one of the two permanent magnets, that is disposed in the downstream side of the ferromagnetic disc.

In FIG. 12 there is illustrated a cross section of an embodiment of the three-in-one rotameter comprising a pair of rotameters 70 and 71 connected to one another in series. It is generally preferred that the two rotameters 70 and 71 have identical tapered flow passages and respectively employ two floats having different values of the weight to volume ratio, which implies that the two floats have the same volume and different weight. It is self evident that the float 73 lighter than the float 72 will rise to a higher position. When equation (1) or (2) applied to each of the two rotameters 70 and 71 are solved simultaneously for the fluid desity $\rho$ by eliminating the volume flow rate $\dot{V}$ that is the same for both rotameters 70 and 71, the following equation is obtained:

$$\rho = \frac{W_2 - W_1 \left[\frac{f(z_1)}{f(z_2)}\right]^2}{V\left\{1 - \left[\frac{f(z_1)}{f(z_2)}\right]^2\right\}}, \quad (4)$$

where $W_1$ and $W_2$ are respectively the weight of the two floats having the same volume V, which are included in the rotameters 70 and 71, respectively, and $z_1$ and $z_2$ are respectively the measured position of the two floats included in the two rotameters 70 and 71. Substitution of the fluid density $\rho$ determined by equation (4) into equation (1) determines the volume flow rate $\dot{V}$ whereupon the mass flow rate $\dot{M}$ is obtained as a product of the volume flow rate $\dot{V}$ and the density $\rho$, which calculation is carried out by a data processor 74 receiving the electrical signals representing the positions $z_1$ and $z_2$ of the two floats as input data. The three-in-one rotameter shown in FIG. 12 measures the mass and volume flow rates as well as the fluid density of fluid flows with unknown fluid density that may or may not vary in time.

In FIG. 13 there is illustrated a cross section of another embodiment of the three-in-one rotameter comprising a pair of rotameters 75 and 76 connected to a common inlet 77 and a common outlet 78 in a parallel arrangement, wherein the two rotameters 75 and 76 have the tapered flow passage of the same geometry and the float of the same volume with different weight. The pressure drop through each of the two rotameter is given by equation $$\Delta P_i = [C + g(z_i)]\dot{V}_i^2, \quad i=1 \text{ and } 2, \quad (5)$$

where C is an empirically determined constant, $g(z_i)$ is an empirically determined function with independent variable $z_i$ that is the position of the float, and the subscript i=1 and 2 stand for the rotameters 75 and 76, respectively. The pressure drop $\Delta P_1$ through the rotameter 75 has to be equal to $\Delta P_2$ through the rotameter 76. Hence equation (5) yields $$\frac{\dot{V}_1^2}{\dot{V}_2^2} = \frac{C + g(z_2)}{C + g(z_1)}. \quad (6)$$

When equation (6) and equation (1) applied to the rotameters 75 and 76 are solved simultaneously for the density $\rho$ of the fluid, the following equation is obtained:

$$\rho = \frac{W_2 - W_1 \frac{C + g(z_1)}{C + G(z_2)} \left[\frac{f(z_1)}{f(z_2)}\right]^2}{V\left(1 - \frac{C + g(z_1)}{C + g(z_2)} \left[\frac{f(z_1)}{f(z_2)}\right]^2\right)}. \quad (7)$$

A data processor equivalent to the element 74 employed in the embodiment shown in FIG. 12 determines $\rho$ as a function of $z_1$ and $z_2$, which also determines the volume flow rate of the fluid, that is equal to the sum of equation (1) applied to the two rotameters 75 and 76, i.e., $$\dot{V} = f(z_1)\sqrt{\frac{2}{C_D}\left(\frac{W_1}{\rho} - V\right)} + F(z_2)\sqrt{\frac{2}{C_D}\left(\frac{W_2}{\rho} - V\right)}. \quad (8)$$

The mass flow rate is obtained by multiplying the density of the fluid given by equation (7) to the volume flow rate given by equation (8).

While the principles of the present invention have now been made clear by the illustrative embodiments, there will be many modifications of the structures, arrangements, proportions, elements and materials, which are obvious to those skilled in the art and particularly adapted to the specific working environments and operating conditions in the practice of the invention without departing from those principles. It is not desired to limit the invention to the particular illustrative embodiments shown and described, and accordingly, all suitable modifications and equivalents may be regarded as falling within the scope of the invention as defined by the claims which follow.

The embodiments of the invention, in which an exclusive property or priviledge is claimed, are defined as follows:

1. An apparatus for measuring flow of fluid media comprising in combination:
   a) a body including a flow passage with cross sectional area progressively increasing from an inlet extremity to an outlet extremity of the flow passage, wherein the outlet extremity of the flow passage is disposed at a higher level than the inlet extremity of the flow passage;
   b) a float including a magnetically reacting element disposed within the flow passage in an arrangement allowing movements in directions parallel to the central axis of the flow passage;
   c) a plurality of float guides of elongated geometry with substantially straight guiding edge disposed parallel to and about the central axis of the flow passage, the guiding edges of the float guides distributed circumferentially about the central axis of the flow passage guiding movements of the float in directions generally parallel to the central axis of the flow passage, wherein at least one of the plurality of float guides has a ridge-like construction extending radially inward from a wall of the flow passage and includes an elongated cavity disposed parallel to the central axis of the flow passage following the guiding edge of the float guide;
   d) a float follower of round geometry including a magnetically reacting element disposed within the elongated cavity included in said at least one float guide in a freely movable arrangement in directions parallel to the central axis of the flow passage, wherein at least one of the float and the float follower includes a magnetic element creating an attractive force between the float and the float follower, whereby the float follower follows movement of the float; and
   e) an optoelectric means providing information on position of the float follower relative to a reference cross section of the flow passage as a measure of flow of fluid media moving through the flow passage.

2. A combination as set forth in claim 1 wherein said combination includes a data processor determining flow rate of the fluid from the information on the position of the float follower.

3. A combination as set forth in claim 1 wherein said combination includes another apparatus having a construction substantially identical to said an apparatus and connected to said an apparatus in a series arrangement connecting outlet of the flow passage of said an apparatus to inlet of the flow passage of said another apparatus, wherein the float included in said an apparatus and the float included in said another apparatus have different values of ratio between weight and volume of the float.

4. A combination as set forth in claim 3 wherein said combination includes a data processor determining at least one of three flow variables including density of fluid, mass flow rate and volume flow rate of the fluid from the information on positions of the two floats respectively included in said an and another apparatus.

5. A combination as set forth in claim 1 wherein said combination includes another apparatus having a construction substantially identical to said an apparatus and connecting a common inlet port to a common outlet port in a parallel arrangement connecting inlets of the flow passages included in said an and another apparatus to the common inlet port and connecting outlets of the flow passages included in said an and another apparatus to the common outlet port, wherein the float included in said an apparatus and the float included in said another apparatus have different values of ratio between weight and volume of the float.

6. A combination as set forth in claim 5 wherein said combination includes a data processor determining at least one of three flow variables including density of fluid, mass flow rate and volume flow rate of the fluid from the information on positions of the two floats respectively included in said an and another apparatus.

7. An apparatus for measuring flow of fluid media comprising in combination:
   a) a first flow passage with cross sectional area progressively increasing from inlet extremity to outlet extremity thereof, wherein the outlet extremity of the first flow passage is disposed at a higher level than the inlet extremity of the first flow passage, said first flow passage including a first float disposed therein in a freely movable arrangement;
   b) first means for determining position of the first float in directions parallel to the central axis of the first flow passage relative to a reference cross section of the first flow passage;
   c) a second flow passage with cross sectional area progressively increasing from inlet extremity to outlet extremity thereof, wherein the outlet extremity of the second flow passage is disposed at a higher level than the inlet extremity of the second flow passage, said second flow passage including a second float disposed therein in a freely movable arrangement; wherein the first and second floats have different values of ratio between weight and volume of the float, and said first and second flow passages are connected to one another in a series arrangement connecting outlet of the first flow passage to inlet of the second flow passage;

d) second means for determining position of the second float in directions parallel to the central axis of the second flow passage relative to a reference cross section of the second flow passage; and e) data processor means for determining one of the three flow variables density, mass flow rate and volume flow rate of fluid moving through the apparatus as a function of the positions of the first and second floats, and determining another of said three flow variables as another function of the positions of the first and second floats.

8. A combination as set forth in claim 7 wherein said combination includes means for determing last of said three flow variables as a further function of the positions of the first and second floats.

9. A combination as set forth in claim 7 wherein each of said first and second means for determining the positions of said first and second floats comprises an electrical means providing an electrical signal representing the position of the float.

10. A combination as set forth in claim 7 wherein each of said first and second means for determining the positions of said first and second floats comprises an optoelectric means providing information on the position of the float.

11. An apparatus for measuring flow of fluid media comprising in combination:

a) a first flow passage with cross sectional area progressively increasing from inlet extremity to outlet extremity thereof, wherein the outlet extremity of the first flow passage is disposed at a higher level than the inlet extremity of the first flow passage, said first flow passage including a first float disposed therein in a freely movable arrangement;

b) first means for determining position of the first float in directions parallel to the central axis of the first flow passage relative to a reference cross section of the first flow passage;

c) a second flow passage with cross sectional area progressively increasing from inlet extremity to outlet extremity thereof, wherein the outlet extremity of the second flow passage is disposed at a higher level than the inlet extremity of the second flow passage, said second flow passage including a second float disposed therein in a freely movable arrangement; wherein the first and second floats have different values of ratio between weight and volume of the float, and said first and second flow passages connects a common inlet port to a common outlet port in a parallel arrangement connecting inlets of the first and second flow passages to the common inlet port and outlets of the first and second flow passages to the common outlet port;

d) second means for determining position of the second float in directions parallel to the central axis of the second flow passage relative to a reference cross section of the second flow passage; and e) data processor means for determining one of the three flow variables density, mass flow rate and volume flow rate of fluid moving through the apparatus as a function of the positions of the first and second floats, and determining another of said three flow variables as another function of the positions of the first and second floats.

12. An apparatus as defined in claim 11 wherein said combination includes means for determining last of said three flow variables as a further function of the positions of the first and second floats.

13. An apparatus as defined in claim 11 wherein each of said first and second means for determining the positions of said first and second floats comprises an electrical means providing an electrical signal representing the position of the float.

14. An apparatus as defined in claim 11 wherein each of said first and second means for determing the positions of said first and second floats comprises an optoelectric means providing information on the position of the float.

* * * * *